United States Patent [19]

Toja et al.

[11] Patent Number: 5,041,436

[45] Date of Patent: Aug. 20, 1991

[54] 1-ARYLSULPHONYL-2-PIPERIDINONE DERIVATIVES, PROCESS AND INTERMEDIATES FOR THE PREPARATION THEREOF, THEIR APPLICATION AS ANTISPASMODICS AND COMPOSITIONS CONTAINING THEM

[75] Inventors: Emilio Toja; Fernando Barzaghi, both of Milan; Giulio Galliani, Monza, all of Italy

[73] Assignee: Roussel Uclaf, Paris, France

[21] Appl. No.: 482,806

[22] Filed: Feb. 21, 1990

[30] Foreign Application Priority Data

Feb. 22, 1989 [IT] Italy ................ 19524 A/89

[51] Int. Cl.$^5$ .......... A61K 31/55; A61K 31/445; C07D 211/96; C07D 401/02
[52] U.S. Cl. .................. 514/212; 514/316; 514/318; 514/319; 514/327; 514/347; 540/597; 546/188; 546/193; 546/216; 546/294; 546/194
[58] Field of Search ........... 546/188, 216, 193, 294, 546/194; 540/597; 514/316, 318, 319, 327, 212, 347

[56] References Cited

U.S. PATENT DOCUMENTS

| | | | |
|---|---|---|---|
| 4,217,130 | 8/1980 | Tsuruta et al. | 548/542 |
| 4,585,769 | 4/1986 | Roger | 514/212 |
| 4,833,156 | 5/1989 | Sakakibara et al. | 414/424 |

FOREIGN PATENT DOCUMENTS

| | | | |
|---|---|---|---|
| 51-110029 | 9/1976 | Japan | 514/327 |
| 63-215624 | 9/1988 | Japan . | |

OTHER PUBLICATIONS

Chem. Abstract, 110:75307d (1989), Sakakibara et al.

*Primary Examiner*—Mary C. Lee
*Assistant Examiner*—Lenora Miltenberger
*Attorney, Agent, or Firm*—Stevens, Davis, Miller & Mosher

[57] ABSTRACT

The invention relates to the products of formula

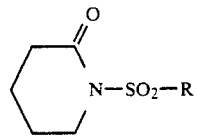

(I)

in which R represents the radical

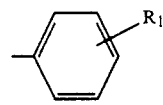

in which $R_1$ at any position on the benzene ring represents linear, branched or cyclic alkyl, alkenyl or alkynyl containing up to 8 carbon atoms, or the radical

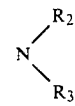

in which $R_2$ and $R_3$, which may be identical or different, represents hydrogen or linear alkyl, alkenyl or alkynyl containing up to 8 carbon atoms or form, together with the nitrogen atom to which they are attached, a carbonaceous heterocyclic radical optionally containing another hetero atom, or the radical OR', R' representing hydrogen, a linear, branched or cyclic alkyl containing up to 8 carbon atoms or aryl containing up to 14 carbon atoms, or the radical $SR_4$ or $S(O)R_5$, $R_4$ and $R_5$ representing linear, branched or cyclic alkyl, alkenyl, or alkynyl containing up to 8 carbon atoms, or R represents naphthyl optionally substituted with the radical $R'_1$, $R'_1$ being as defined above for $R_1$, to a process and intermediates for the preparation thereof, to their application as medicinal products and to compositions containing them.

14 Claims, No Drawings

1-ARYLSULPHONYL-2-PIPERIDINONE DERIVATIVES, PROCESS AND INTERMEDIATES FOR THE PREPARATION THEREOF, THEIR APPLICATION AS ANTISPASMODICS AND COMPOSITIONS CONTAINING THEM

The present invention relates to new 1-arylsulphonyl-2-piperidinone derivatives, to a process and intermediates for the preparation thereof, to their application as medicinal products and to compositions containing them.

The subject of the invention is the compounds of formula (I):

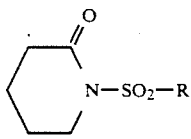

(I)

in which R represents the radical

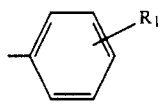

in which $R_1$ at any position on the benzene ring represents linear, branched or cyclic alkyl, alkenyl or alkynyl containing up to 8 carbon atoms, or the radical

in which $R_2$ and $R_3$, which may be identical or different, represent hydrogen or linear alkyl, alkenyl or alkynyl containing up to 8 carbon atoms or form, together with the nitrogen atom to which they are attached, a carbonaceous heterocyclic radical optionally containing another hetero atom, or the radical OR', R' representing hydrogen, a linear, branched or cyclic alkyl containing up to 8 carbon atoms or aryl containing up to 14 carbon atoms, or the radical $SR_4$ or $S(O)R_5$, $R_4$ and $R_5$ representing linear, branched or cyclic alkyl, alkenyl, or alkynyl containing up to 8 carbon atoms, or R represents naphthyl optionally substituted with the radical $R'_1$, $R'_1$ being as defined above for $R_1$.

Alkyl is preferably alkyl containing from 1 to 6 carbon atoms, for example methyl, ethyl, n-propyl, isopropyl, n-butyl, isobutyl, tertbutyl, n-pentyl, n-hexyl, cyclopropyl, cyclobutyl, cyclopentyl or cyclohexyl.

Unsaturated alkyl is preferably ethenyl propenyl or butenyl.

When $R_2$ and $R_3$ form, with the nitrogen atom to which they are attached, a heterocyclic radical optionally containing another hetero atom, the radical in question is preferably piperidyl, piperazinyl, morpholinyl, pyrrolidinyl, hexahydroazepine or octahydroazocine.

Aryl is preferably phenyl or naphthyl.

Among preferred compounds of the invention, there may be mentioned the compounds in which R represents the radical

$R_1$ retaining the same meaning as above, and most especially those in which $R_1$ is at the 4-position, and those in which $R_1$ represents the radical

in which $R'_2$ and $R'_3$, which may be identical or different, represent linear or branched alkyl containing up to 8 carbon atoms or form, with the nitrogen atom to which they are attached, a heterocyclic radical.

Among the preferred compounds of the invention, there may be mentioned most especially the compounds in which $R'_1$ and $R'_2$, which may be identical or different, represent alkyl containing up to 4 carbon atoms, as well as those in which $R_1$ represents a piperidinyl or hexahydroazepinyl.

The subject of the invention is more especially the compounds whose preparation is given below in the Examples, and most especially the compound of Examples 2, 4 or 5.

The compounds of formula (I) display advantageous pharmacological properties, and in particular a specific and selective antimuscarinic activity.

The subject of the invention is hence the products of formula (I) as medicinal products useful, in particular, for the antispasmodic treatment of muscle spasms in gastroenterology, in gynecology, in obstetrics, in urology, in hepatology and in radiology.

The subject of the invention is more especially, as a medicinal product, the preferred compounds mentioned above, and most especially the product of Examples 2, 4 or 5.

The usual dosage is variable according to the condition in question, the subject treated and the administration route; it can be between 10 mg and 1 g per day, and preferably between 20 mg and 100 mg per day, for example between 30 and 60 mg per day in one or more doses for the product of Example 2 administered orally.

The subject of the present invention is also pharmaceutical compositions containing, as active principle, at least one product of formula (I). The pharmaceutical compositions of the invention can be solid or liquid, and be presented in the pharmaceutical dosage forms commonly used in human medicine, such as, for example, simple or sugar-coated tablets, hard gelatin capsules, granules, suppositories or injectable preparations; they are prepared according to the usual methods.

The active principle or principles may be incorporated therein with excipients customarily employed in these pharmaceutical compositions, such as talc, gum arabic, lactose, starch, magnesium stearate, cocoa butter, aqueous or non-aqueous vehicles, fats of animal or vegetable origin, paraffinic derivatives, glycols, various wetting, dispersant or emulsifying agents and preservatives.

The subject of the invention is also a process for preparing the compounds of formula (I), characterized in that a compound of formula (II):

$$R-SO_2-Hal \quad (II)$$

in which Hal represents chlorine or bromine and R retains the meaning stated above, is subjected to the action of 5-aminovaleric acid (II):

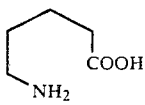 (III)

to obtain a compound of formula (IV):

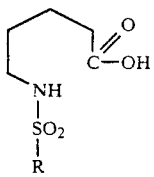 (IV)

which is cyclized to obtain the corresponding product of formula (I).

In a preferred embodiment of the process of the invention:

the condensation of the compound (II) with 5-aminovaleric acid is carried out under classical Schotten-Baumann conditions, in the presence of a base such as sodium hydroxide or potassium hydroxide for example in an organic solvent such as tetrahydrofuran.

The cyclization of the compound of formula (IV) is carried out by means of an acid anhydride such as acetic anhydride, or alternatively by means of other condensing agents such as sulphuric acid, phosphoric anhydride, phosphoric acid, metaphosphoric acid, dicyclohexyl- carbodiimide in the presence of pyridine or bis(trimethylsilyl) amine with trimethylsilyl chloride.

The compounds of formula (II) used as starting materials are, generally speaking, known [see Houben Weyl, 4th ed., vol. 9, Ch 18 (1955)].

The preparation of the products used as starting materials for Examples 3, 4, 5 and 6 is described below.

The compounds of formula (IV) obtained on implementation of the process of the invention are new products, and are in themselves a subject of the present invention.

The examples which follow illustrate the invention without, however, limiting the latter.

EXAMPLE 1

1-[4-(Dimethylamino)benzenesulphonyl]-2-piperidinone

Stage A:

5-(4-Dimethylaminobenzenesulphonylamino)valeric acid 4.4 g of 4-dimethylaminobenzenesulphonyl chloride (Chem. Ber. 43, 3038, (1910)) are added to a solution comprising 2.34 g of 5-aminovaleric acid and 2.4 g of sodium hydroxide dissolved in 24 cm³ of water, followed by the addition of 24 cm³ of tetrahydrofuran in order to obtain a solution. The temperature rises to 36° C. The mixture is kept stirring for 4 hours, the tetrahydrofuran is evaporated off, the reaction medium is acidified using acetic acid and extracted with chloroform, the organic phase is dried and the solvents are removed under reduced pressure. 3.7 g of expected product are obtained. M.p. 105°–110° C. After crystallization in an isopropanol/water mixture (1:1), the product, melting point 118°–120° C., is obtained.

Analysis: $C_{13}H_{20}N_2O_4S$

| | | | |
|---|---|---|---|
| Calculated: | C % 51.98 | H % 6.71 | N % 9.33 |
| Found: | 51.85 | 6.77 | 9.28 |

Stage B:

1-[4-(Dimethylamino)benzenesulphonyl]-2-piperidinone 4.8 g of product obtained in stage A is heated to reflux for 3 hours with 4.8 g of sodium acetate in 48 cm³ of acetic anhydride. The mixture is cooled to room temperature and evaporated to dryness, the residue is taken up in 50 cm³ of water, filtered off and dried and 3.7 g of expected crude product are obtained. M.p. 165°–170° C. After crystallization in ethanol, 2.9 g of pure product are obtained. M.p. 169°–171° C.

Analysis: $C_{13}H_{18}N_2O_3S$

| | | | |
|---|---|---|---|
| Calculated: | C % 55.30 | H % 6.43 | N % 9.92 |
| Found: | 55.5 | 6.5 | 9.8 |

EXAMPLE 2

1-[4-(Diethylamino)benzenesulphonyl]-2-piperidinone

Stage A:

5-(4-Diethylaminobenzenesulphonylamino)valeric acid 2.5 g of 4-diethylaminobenzenesulphonyl chloride are added to a solution comprising 1.17 g of 5-aminovaleric acid and 1.2 g of sodium hydroxide dissolved in 12 cm³ of water, followed by the addition of 12 cm³ of tetrahydrofuran in order to obtain a solution. The mixture is kept stirring for 2 hours at room temperature, the tetrahydrofuran is evaporated off, the reaction medium is acidified using acetic acid and extracted with chloroform, the organic phase is dried and the solvents are removed under reduced pressure. 2.2 g of expected product are obtained. M.p. 106°–108° C. After crystallization in an isopropanol/water mixture (1:1), the product, melting point 109°–110° C., is obtained.

Analysis: $C_{15}H_{24}N_2O_4S$

| | | | |
|---|---|---|---|
| Calculated: | C % 54.86 | H % 7.36 | N % 8.53 |
| Found: | 54.63 | 7.28 | 8.65 |

Stage B:

1-[4-(Diethylamino)benzenesulphonyl]-2-piperidinone 2 g of product obtained in stage A are heated to reflux for 2 hours with 2 g of sodium acetate in 20 cm³ of acetic anhydride. The mixture is cooled to room temperature and evaporated to dryness, the residue is taken up in a mixture of chloroform and water, the organic phase is separated and dried and, after removal of the solvents, 1.8 g of expected crude product are obtained. M.p. 118°–120° C. After crystallization in isopropanol, 1.2 g of pure product are obtained. M.p. 122°–123° C.

Analysis: $C_{15}H_{22}N_2O_3S$

| | | | |
|---|---|---|---|
| Calculated: | C % 58.04 | H % 7.14 | N % 9.02 |

| -continued | | | |
|---|---|---|---|
| Found: | 58.28 | 7.34 | 9.09 |

4-(diethylamino)benzenesulphonyl chloride used as a starting material was prepared as described in the European Patent Application published under No. 0,033,578.

EXAMPLE 3

1-[4-(Dipropylamino)benzenesulphonyl]-2-piperidinone

Stage A:
5-(4-Dipropylaminobenzenesulphonylamino)valeric acid 6.5 g of 4-dipropylaminobenzenesulphonyl chloride, in solution, are added to a solution comprising 2.76 g of 5-aminovaleric acid and 2.82 g of sodium hydroxide dissolved in 28 cm$^3$ of water, followed by the addition of 28 cm$^3$ of tetrahydrofuran. The mixture is kept stirring for 2 hours, the tetrahydrofuran is evaporated off, the reaction medium is acidified using acetic acid and the solid formed is filtered off, washed with water and dried. 6 g of expected product are obtained. M.p. 95°–98° C. After crystallization in an isopropanol/water mixture (1:1), 5 g of product, melting point 98°–99° C., are obtained.

Analysis: $C_{17}H_{28}N_2O_4S$

| Calculated: | C % 57.28 | H % 7.92 | N % 7.86 |
|---|---|---|---|
| Found: | 57.34 | 8.0 | 7.91 |

Stage B
1-[4-(Dipropylamino)benzenesulphonyl]-2-piperidinone 5 g of product obtained in Stage A are heated to reflux for 2 hours with 5 g of sodium acetate in 50 cm$^3$ of acetic anhydride. The mixture is cooled to room temperature and evaporated to dryness, the residue is taken up in 50 cm$^3$ of water and dried and 4.4 g of expected product are obtained. M.p. 105°–108° C. after chromatography on silica (eluent: ethyl acetate/n-hexane, 1:1). After crystallization in isopropanol, 3.2 g of pure product are obtained. M.p. 110°–111° C.

Analysis: $C_{17}H_{26}N_2O_3S$

| Calculated: | C % 60.32 | H % 7.74 | N % 8.28 |
|---|---|---|---|
| Found: | 60.48 | 7.81 | 8.36 |

4-Dipropylaminobenzenesulphonyl chloride was prepared as follows:

10.2 g of N,N-dipropylaniline (Annalen der Chemie 214, 168) are added at a temperature of between +5° and +10° C. to a solution comprising 10.86 g (equivalent to 8.86 cm$^3$) of trimethylsilyl chlorosulphonate and 50 cm$^3$ of dichloromethane. The mixture is allowed to return to room temperature and is evaporated to dryness, the residue is taken up in acetone and the solid product is filtered off and dried. 4.9 g of acid are obtained, which product is taken up in 100 cm$^3$ of dichloromethane, 2.63 g of phosphorus pentachloride are added and the mixture is heated to reflux for 4 hours. It is cooled to room temperature and evaporated to dryness and the residual oil is taken up in benzene and water. The organic phase is separated and dried and the solvents are evaporated off. 4.5 g of oil are obtained, which product is used as it is for the next stage.

EXAMPLE 4

1-[4-(1-Piperidinyl)benzenesulphonyl]-2-piperidinone

Stage A:
5-(4-Piperidinylbenzenesulphonylamino)valeric acid 7.8 g of 4-piperidinylbenzenesulphonyl chloride are added to a solution comprising 3.51 g of 5-aminovaleric acid and 3.6 g of sodium hydroxide dissolved in 35 cm$^3$ of water, followed by the addition of 35 cm$^3$ of tetrahydrofuran in order to obtain a solution. The temperature rises to 35° C. The mixture is kept stirring for 4 hours at room temperature, the tetrahydrofuran is evaporated off, the reaction medium is acidified using acetic acid, diluted with 100 cm$^3$ of water and extracted with chloroform, the organic phase is dried and the solvents are removed under reduced pressure. 5.8 g of expected product are obtained. M.p. 115°–120° C. After crystallization in an isopropanol/water mixture (1:1), the product, melting point 120°–122° C., is obtained.

Analysis: $C_{16}H_{24}N_2O_4S$

| Calculated: | C % 56.45 | H % 7.10 | N % 8.23 |
|---|---|---|---|
| Found: | 56.19 | 7.05 | 8.06 |

Stage B:
1-[4-(1-Piperidinyl)benzenesulphonyl]-2-piperidinone 5 g of product obtained in Stage A are heated to reflux for 4 hours with 5 g of sodium acetate in 50 cm$^3$ of acetic anhydride. The mixture is cooled to room temperature and evaporated to dryness, the residue is taken up in 50 cm$^3$ of water, filtered off and dried and 4.4 g of expected crude product are obtained. M.p. 140°–145° C. After crystallization in ethanol, 3.4 g of pure product are obtained. M.p. 145°–146° C.

Analysis: $C_{16}H_{22}N_2O_3S$

| Calculated: | C % 59.60 | H % 6.88 | N % 8.69 |
|---|---|---|---|
| Found: | 59.51 | 6.97 | 8.63 |

4-Piperidinylbenzenesulphonyl chloride was prepared as follows:

To a solution, cooled to between 0° C. and −5° C., comprising 8.46 g of sulphur trioxide in 45 cm$^3$ of methylene chloride, there are added dropwise 9.3 g of dioxane followed by 17.1 g of N-phenylpiperidine dissolved in 45 cm$^3$ of methylene chloride. The mixture is allowed to return to room temperature, then heated to reflux for 1 hour and evaporated to dryness, the residue is neutralized with 10% strength sodium carbonate solution, the aqueous phase is concentrated and the residue is dried and treated with 200 cm$^3$ of phosphoryl chloride and 21.8 g of phosphorus pentachloride for 12 hours at room temperature. The mixture is evaporated to dryness, the residue is taken up in chloroform with a little water, the organic phase is separated, dried over sodium sulphate and filtered and the solvent is evaporated off. 19 g of expected product are obtained, which product is used as it is in the next stage.

EXAMPLE 5

1-[4-(1-Hexahydroazepinyl)benzenesulphonyl]-2-piperidinone

Stage A:
5-[4-(1-Hexahydroazepinyl)benzenesulphonylamino]-valeric acid 6 g of 4-hexahydroazepinylbenzenesulphonyl chloride are added to a solution comprising 2.56 g of 5-aminovaleric acid and 2.63 g of sodium hydroxide dissolved in 60 cm$^3$ of water, followed by the addition of 60 cm$^3$ of tetrahydrofuran in order to obtain a solution. The mixture is kept stirring for 2 hours at room temperature, the tetrahydrofuran is evaporated off, the reaction medium is acidified using acetic acid, the precipitate is filtered off, washed with water and dried and 4.65 g of expected product are obtained. M.p. 135°–140° C. After crystallization in isopropanol, the product, melting point 139°–140° C., is obtained.

Analysis: $C_{17}H_{26}N_2O_4S$

| | | | |
|---|---|---|---|
| Calculated: | C % 57.60 | H % 7.39 | N % 7.90 |
| Found: | 57.46 | 7.37 | 7.98 |

Stage B:
1-[4-(1-Hexahydroazepinyl)benzenesulphonyl]-2-piperidinone 4 g of product obtained in stage A are heated to reflux for 1 hour with 4 g of sodium acetate in 80 cm$^3$ of acetic anhydride. The mixture is cooled to room temperature and evaporated to dryness, the residue is taken up in 60 cm$^3$ of water, filtered and dried and 3.5 g of expected product are obtained. After crystallization in isopropanol, 2.3 g of product are obtained. M.p. 164°–165° C.

Analysis: $C_{17}H_{24}N_2O_3S$

| | | | |
|---|---|---|---|
| Calculated: | C % 60.69 | H % 7.19 | N % 8.33 |
| Found: | 60.75 | 7.09 | 8.41 |

4-Hexahydroazepinylbenzenesulphonyl chloride was prepared as follows:

To a solution, cooled to between +5° C. and +10° C., comprising 2.64 g of sulphur trioxide in 78 cm$^3$ of methylene chloride, there are added dropwise 2.91 g of dioxane followed by 5.26 g of 1-phenylhexahydroazepine (Tetrahedron 41 (1985) p. 101–106) in 53 cm$^3$ of methylene chloride. The mixture is allowed to return to room temperature, then heated to reflux for 2 hours and cooled again to room temperature, 200 cm$^3$ of ethyl ether are added to the suspension, the precipitate is filtered off, washed with ether and dried and 7.2 g of acid (m.p. 235° C., decomp.) are obtained, which acid is treated with 36 cm$^3$ of phosphoryl chloride in 36 cm$^3$ of methylene chloride and with 5.87 g of phosphorus pentachloride for 4 hours at room temperature. The mixture is evaporated to dryness, the residue is taken up with 100 cm$^3$ of water and 150 cm$^3$ of chloroform, the organic phase is separated, dried over sodium sulphate and filtered and the solvent is evaporated off. 6.6 g of expected product are obtained. M.p. 85°–88° C.

EXAMPLE 6

1-[4-(1-Azacyclooctyl)benzenesulphonyl]-2-piperidinone

Stage A:
5-[4-(1-Azacyclooctyl)benzenesulphonylamino]valeric acid 4.5 g of 4-azacyclooctylbenzenesulphonyl chloride are added to a solution comprising 1.82 g of 5-aminovaleric acid and 1.87 g of sodium hydroxide dissolved in 45 cm$^3$ of water, followed by the addition of 45 cm$^3$ of tetrahydrofuran in order to obtain a solution. The mixture is kept stirred for 2 hours at room temperature, the tetrahydrofuran is evaporated off, the reaction medium is acidified using acetic acid, the precipitate is filtered off, washed with water and dried and 3.6 g of expected product are obtained. M.p. 149°–150° C. After crystallization in an isopropanol/water mixture (1:1), the product, melting point 153°–154° C., is obtained.

Analysis: $C_{18}H_{28}N_2O_4S$

| | | | |
|---|---|---|---|
| Calculated: | C % 58.67 | H % 7.66 | N % 7.60 |
| Found: | 58.76 | 7.56 | 7.74 |

Stage B:
1-[4-(1-Azacyclooctyl)benzenesulphonyl]-2-piperidinone 3.4 g of product obtained in stage A are heated to reflux for 1 hour with 3.4 g of sodium acetate in 68 cm$^3$ of acetic anhydride. The mixture is cooled to room temperature and evaporated to dryness, the residue is taken up in 50 cm$^3$ of water, filtered off and dried and 2.87 g of expected product are obtained. M.p. 150°–152° C. After crystallization in isopropanol, 1.9 g of pure product are obtained. M.p. 152°–153° C.

Analysis: $C_{18}H_{26}N_2O_3S$

| | | | |
|---|---|---|---|
| Calculated: | C % 61.68 | H % 7.48 | N % 7.99 |
| Found: | 61.50 | 7.50 | 7.86 |

4-Azacyclooctylbenzenesulphonyl chloride was prepared as follows:

Stage A: 1-Azacyclooctylbenzene 4.3 g of sodium amide at a concentration of 50% in toluene, suspended in 18.9 cm$^3$ (equivalent to 16.9 g) of heptamethylenamine, are heated to 100° C. for 20 minutes, and 7.85 g (equivalent to 5.03 cm$^3$) of bromobenzene are then added dropwise. The reaction medium is heated to reflux for 18 hours and cooled to room temperature, and 50 cm$^3$ of water are added. 100 cm$^3$ of benzene are added, the organic phase is separated, extracted using 5% strength aqueous hydrochloric acid solution and alkalinized using 20% strength aqueous sodium hydroxide solution, the oil phase is separated, extracted with ethyl ether and dried and the solvent is evaporated off. After distillation of the residue (b.p. 118°–120° C. at 0.5 mm Hg), 9.4 g of expected product are obtained.

Analysis: $C_{13}H_{19}N$

| | | | |
|---|---|---|---|
| Calculated: | C % 82.48 | H % 10.12 | N % 7.40 |

|        |       |      |      |
|--------|-------|------|------|
| Found: | 82.28 | 9.95 | 7.52 |

Stage B: 4-Azacyclooctylbenzenesulphonyl chloride.

To a solution comprising 3.97 g of sulphur trioxide in 40 cm³ of methylene chloride and cooled to between +5° C. and +10° C., there are added dropwise 4.36 g of dioxane followed by 9.4 g of 1-azacyclooctylbenzene. The mixture is allowed to return to room temperature and then heated to reflux for 1 hour. It is cooled again to room temperature, diluted with 200 cm³ of ethyl ether and filtered and, after drying, 13.3 g of acid are obtained, which acid is treated with 10.34 g of phosphorus pentachloride in 50 cm³ of phosphoryl chloride and 50 cm³ of methylene chloride for 3 hours at room temperature. The mixture is evaporated to dryness, the residue is taken up with water and chloroform, and the organic phase is separated, dried over sodium sulphate, filtered and evaporated. 13 g of expected product are obtained.

EXAMPLES OF PHARMACEUTICAL COMPOSITIONS a) Tablets corresponding to the following formula were prepared:
Product of Example 2 ... 10 mg
Excipient q.s. for a finished tablet weighing ... 300 mg
(Details of the excipient: lactose, wheat starch, treated starch, rice starch, magnesium stearate, talc).

b) Hard gelatin capsules corresponding to the following formula were prepared:
Product of Example 4 ... 20 mg
Excipient q.s. for a finished hard gelatin capsule weighing ... 300 mg
(Details of the excipient: talc, magnesium stearate, Aerosil).

BIOCHEMICAL AND PHARMACOLOGICAL STUDIES

1) Binding to different brain receptors.

A) Muscarinic receptor 1

Preparation of this is carried out from cortices removed from the brains of male rats weighing 150 to 200 g (Iffa Credo), ground in a Polytron in a 10 mM Na/K buffer pH 7.4. After incubation (0.5 ml aliquots of homogenate) for 60 minutes at 25° C. in the presence of 0.25 nM [³H]pirenzepine, either alone, or with the test product, or with an excess of $10^{-5}$M pirenzepine (to determine the non-specifically bound radioactivity), the incubates are cooled and filtered.

The filtration is performed on Whatman GF/C filters prewashed in a 0.05% strength solution of polyethylenimine. The filters are rinsed with 3×5 ml of 10 mM Na/K phosphate buffer pH 7.4 and the measurements are then performed by liquid scintillation.

b) Muscarinic receptor 2

The preparation is performed from brains of male rats weighing 150 to 200 g (Iffa Credo).

The brains are ground (Teflon-glass) in 0.32M sucrose solution. The homogenate is centrifuged for 10 minutes at 1,000 g (0°-4° C.)

The supernatant obtained is collected and centrifuged at 30,000 g for 15 minutes (0°-4° C.).

The regulus is resuspended in 50 mM Tris buffer pH 7.5 and the new homogenate is centrifuged again at 30,000 g for 15 minutes (0°-4° C.).

After removal of the supernatant, the regulus may be used immediately or stored for up to 1 month at −30° C.

For an experiment, the regulus are first thawed, if necessary, at room temperature and resuspended using a Dounce in 50 mM Tris buffer pH 7.5. 2 ml aliquots are incubated for 60 minutes at 25° C. in the presence of 0.3 nM [³H]quinuclidinyl benzylate, either alone, or with the test product, or with $10^{-5}$M benzatropine to determine the non-specifically bound radioactivity.

At the end of the incubation period, the incubate tubes are cooled to 4° C. and filtered rapidly on Whatman GF/C filters. The filters are rinsed with 3×5 ml of 50 nM Tris buffer pH 7.5 and the measurements are then performed by liquid scintillation (Henry I. Yamamura, Solomon H. Snyder, Proc. Nat. Acad. Sc. (1974) 71, No. 5, 1725-1729).

The results are expressed as an $IC_{50}$ (concentration needed to inhibit by 50% the specifically bound radioactivity).

TABLE 1

| Compound of Example | Affinity for $M_1$ and $M_2$ muscarinic receptors | |
|---|---|---|
| | [³H]pirenzepine | [³H]quinuclidinyl benzylate |
| 2 | 314 | 4,600 |
| 4 | 128 | 2,240 |
| 5 | 49 | 660 |

The compounds of Examples 2, 4 and 5 show a noteworthy advantageous affinity for the muscarinic receptor, and mainly for the $M_1$ type receptor. In contrast, the same compounds showed negligible affinity ($IC_{50}$ >5,000–10,000) for the other receptors examined, including those for dopamine, histamine, serotonin (5-$HT_1$ and 5-$HT_2$), benzodiazepines, GABA, adrenoreceptors (alpha$_1$, alpha$_2$, beta$_1$, beta$_2$) or alternatively opiate receptors (mu, kappa).

2) Interaction and Affinity with Different Intestinal Receptors

The interaction of the compounds with different receptors was assessed on isolated guinea pig ileum according to the following method.

Guinea pig ileum segments measuring 2.5–3 cm were washed and immediately suspended in a bath containing 10 ml of Tyrode's solution at 37° C. aerated with a mixture of oxygen (95%) and carbon dioxide (5%). After a stabilization period of at least 30 minutes, the contractions were recorded, maintaining the preparation under constant tension of 1 g using a gauge connected to a polygraph. The agonist action was assessed by leaving the compound in contact with the isolated tissue for a period necessary for expressing the maximal contraction; the preparation was then washed with Tyrode's solution. The next dose was added to the bath only after the preparation had returned to its base line. As a reference product, arecoline was employed. The antagonist action was assessed on contractions induced by acetyl choline ($1 \times 10^{-6}$M), histamine ($1 \times 10^{-5}$M) and barium chloride ($2 \times 10^{-4}$M). Atropine, diphenhydramine and papaverine were emplohyed as reference products. The contact time before adding the agonist was one minute.

For each compound, the dose-response curves are obtained with 4 to 6 different concentrations and 3 to 5 independent tests. The agonist activity is expressed by pD$_2$ (negative logarithm of the dose which produces 50% of maximum effect). The antagonist activity is expressed by IC$_{50}$ (concentration inhibiting 50% of the maximal response).

The results obtained with the compounds of Examples 2, 4 and 5 are recorded in the following table:

TABLE 2

| Compound of Example | Antagonist to different agents (IC$_{50}$:M) | | | Agonist action pD$_2$ |
| --- | --- | --- | --- | --- |
| | ACh | Histam. | BaCl$_2$ | |
| 2 | $9.3 \times 10^{-7}$ | $>10^{-5}$ | $>10^{-5}$ | $<5$ |
| 4 | $1.5 \times 10^{-6}$ | $>10^{-5}$ | $>10^{-5}$ | $<5$ |
| 5 | $2.7 \times 10^{-7}$ | $>10^{-5}$ | $>10^{-5}$ | $<5$ |
| Atropine | $9.5 \times 10^{-9}$ | | | |
| Diphenydramine | | $8.3 \times 10^{-7}$ | | |
| Papaverine | | | $4.5 \times 10^{-5}$ | |
| Arecoline | | | | 6.68 |

The "in vitro" studies on isolated guinea pig ileum demonstrated that the compounds of the invention are antimuscarinic agents. They antagonize contractions induced by acetyl choline, but not those induced by histamine and barium chloride.

3) "In Vivo" Anticholinergic Action

The anticholinergic activity of the compounds was determined by assessing the capacity to inhibit the cholinomimetic effects induced by carbachol. Atropine sulphate was employed as a reference product.

CD$_1$ male mice weighing 25 to 30 g were used. They were distributed in groups of 6 animals and treated intraperitoneally with scalar doses of the products or 0.25% Methocel for the controls. 12 animals were used for each dose. 30 minutes after administration of the compounds, the mice were injected subcutaneously with 1 mg/kg of carbachol dissolved in physiological saline.

Each animal was examined 30 minutes after the injection of carbachol to assess the presence of diarrhoea, salivation and eye watering; in addition, the body temperature was measured by means of a thermocouple inserted 1.5 cm into the rectum.

Carbachol (1 mg/kg s.c.) induced diarrhoea, salivation and eye watering in all the control mice, and a decrease in rectal temperature of approximately 2.5° C.

For each compound, we have determined and recorded in the following table the dose capable of inhibiting the appearance of the carbachol-induced cholinometric symptoms in 50% of the animals, and of increasing by 1° C. the hypothermic effect induced by the cholinergic agent.

TABLE 3

| Compound of Example | Dose mg/kg i.p. | | | Body temperature |
| --- | --- | --- | --- | --- |
| | Diarrhoea | Salivation | Eye watering | |
| 2 | 5 | >50 | >50 | >50 |
| 4 | 6 | >50 | >50 | >50 |
| 5 | 2 | ≈25 | >50 | 50 |
| Atropine | 0.04 | 0.06 | 0.05 | 0.03 |

The results obtained show that, in contrast to atropine, the compounds exert "in vivo" a selective anticholinergic action in respect of the intestinal musculature.

What is claimed is:

1. The compound of formula (I):

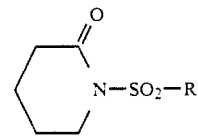

(I)

in which R represents the radical

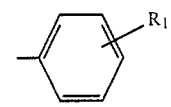

in which R$_1$ at any position on the benzene ring represents linear, branched or cyclic alkyl, alkenyl or alkynyl containing up to 8 carbon atoms, or the radical

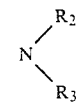

in which R$_2$ and R$_3$, which may be identical or different, represent hydrogen or linear alkyl, alkenyl or alkynyl containing up to 8 carbon atoms or form, together with the nitrogen atom to which they are attached, a piperidinyl or hexahydroazepinyl radical, or the radical OR', R' representing hydrogen, a linear, branched or cyclic alkyl containing up to 8 carbon atoms or aryl containing up to 14 carbon atoms, or the radical SR$_4$ or S(O)R$_5$, R$_4$ and R$_5$ representing linear, branched or cyclic alkyl, alkenyl, or alkynyl containing up to 8 carbon atoms, or R represents naphthyl optionally substituted with the radical R'$_1$, R'$_1$ being as defined above for R$_1$.

2. The compounds of formula (I) as defined in claim 1, in which R represents the radical

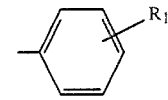

R$_1$ having the same means as in claim 1.

3. The compounds of formula (I) as defined in claim 2, in which the radical R$_1$ is at the 4-position.

4. The compound of formula (I)

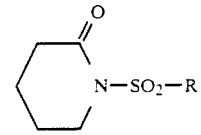

(I)

in which R represents the radical

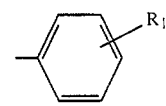

in which $R_1$ at any position on the benzene ring represents the radical

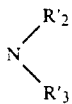

in which $R'_2$ and $R'_3$, which may be identical or different, represent a linear or branched alkyl containing up to 8 carbon atoms or form, with the nitrogen atom to which they are attached, a piperidinyl or hexahydroazepinyl radical.

5. The compounds of formula (I) as defined in claim 4, in which $R'_2$ and $R'_3$, which may be identical or different, represent alkyl containing up to 4 carbon atoms.

6. The compounds of formula (I) as defined in claim 4, in which $R_1$ represents a piperidinyl radical.

7. The compounds of formula (I) as defined in claim 4, in which $R_1$ represents a hexahydroazepinyl radical.

8. A compound selected from the group consisting of:
1-[4(diethylamino)benzenesulphonyl]-2-piperidione;
1-[4(1-piperidinyl)benzenesulphonyl]-2-piperidinone; and
1-[4(1-hexahydroazepinyl)benzenesulphonyl]-2-piperidinone.

9. A therapeutic composition for the treatment of a patient suffering from muscle spasms, comprising an anti-spasmodically effective amount of a compound as defined in claim 1 and a pharmacologically acceptable carrier.

10. A therapeutic composition for the treatment of a patient suffering from muscle spasms, comprising an anti-spasmodically effective amount of a compound as defined in claim 8 and a pharmacologically acceptable carrier.

11. A method of treating a patient suffering from muscle spasms comprising administering to the patient an anti-spasmodically effective amount of a compound as defined in claim 1.

12. A method of treating a patient suffering from muscle spasms comprising administering to the patient an anti-spasmodically effective amount of a compound as defined in claim 8.

13. A therapeutic composition for the treatment of a patient suffering from muscle spasms, comprising an anti-spasmodically effective amount of a compound as defined in claim 4 and a pharmacologically acceptable carrier.

14. A method of treating a patient suffering from muscle spasms comprising administering to the patient an anti-spasmodically effective amount of a compound as defined in claim 4.

* * * * *